US012668596B2

(12) United States Patent
Huntley

(10) Patent No.: US 12,668,596 B2
(45) Date of Patent: Jun. 30, 2026

(54) PROCESS FOR CRYSTALLIZING NALMEFENE HYDROCHLORIDE

(71) Applicant: RHODES TECHNOLOGIES, Coventry, RI (US)

(72) Inventor: C. Frederick M. Huntley, East Greenwich, RI (US)

(73) Assignee: RHODES TECHNOLOGIES, Coventry, RI (US)

( * ) Notice: Subject to any disclaimer, the term of this patent is extended or adjusted under 35 U.S.C. 154(b) by 521 days.

(21) Appl. No.: 18/260,951

(22) PCT Filed: Jan. 27, 2022

(86) PCT No.: PCT/US2022/014104

§ 371 (c)(1),
(2) Date: Jul. 11, 2023

(87) PCT Pub. No.: WO2022/165040

PCT Pub. Date: Aug. 4, 2022

(65) Prior Publication Data

US 2024/0109907 A1 Apr. 4, 2024

Related U.S. Application Data

(60) Provisional application No. 63/142,791, filed on Jan. 28, 2021.

(51) Int. Cl.
*C07D 489/08* (2006.01)

(52) U.S. Cl.
CPC .................................. *C07D 489/08* (2013.01)

(58) Field of Classification Search
CPC .................................................... C07D 489/08
See application file for complete search history.

(56) References Cited

U.S. PATENT DOCUMENTS 4,535,157 A 8/1985 Meltzer et al.
4,751,307 A 6/1988 White et al.
8,598,352 B2 12/2013 De Faveri et al.
8,754,217 B2 6/2014 Lopez De Diego et al.
2014/0296525 A1 10/2014 De Faveri et al.

FOREIGN PATENT DOCUMENTS

CN 106167492 A 11/2016
RU 2712232 C1 1/2020
WO WO-2010136039 A1 12/2010
WO WO-2013083685 A1 6/2013

OTHER PUBLICATIONS

Karhuvaara, S., et al., "Targeted nalmefene with simple medical management in the treatment of heavy drinkers: a randomized double-blind placebo-controlled multicenter study," Alcohol. Clin. Exp. Res. 31(7):1179-1187, Wiley, United Kingdom (Apr. 2007).
Hahn, E.F., et al., "Narcotic antagonists. 4. Carbon-6 derivatives of N-substituted noroxymorphones as narcotic antagonists," J. Med. Chem. 18(3):259-262, ACS Publications, United States (1975).
Caira, M.R., et al., "Preparation and crystal characterization of a polymorph, a monohydrate, and an ethyl acetate solvate of the antifungal fluconazole," J. Pharm. Sci. 93(3):601-611, Wiley-Liss, Inc., United States (Mar. 2004).
Van Tonder, E.C., et al., "Preparation and physicochemical characterization of 5 niclosamide solvates and 1 hemisolvate," AAPS Pharm Sci Tech 5(1):E12, Springer International Publishing AG, Switzerland (2004) (10 pages).
Bingham, A. L., et al., "Over one hundred solvates of sulfathiazole," Chemical Communications (7):603-604, Royal Society of Chemistry, United Kingdom (2001).
"Molecular Structure, Properties, and States of Matter" in Remington's Pharmaceutical Sciences, Chapter 13, pp. 172-174,18th ed, Gennaro, A. R. ed., Mack Publishing Co., Easton PA, United States (1990).
International Search Report and Written Opinion for International Application No. PCT/US2022/014104, European Patent Office, Netherlands, mailed on Apr. 8, 2022, 10 pages.
Brittain, H., "Nalmefene Hydrochloride," in Analytical Profiles of Drug Substances and Excipients, vol. 24, pp. 351-395, Academic Press Inc., United States (1996).

*Primary Examiner* — Alicia L Otton

(57) ABSTRACT

The application is directed to an efficient process for crystallizing nalmefene hydrochloride in a hydrated form from an aqueous hydrochloric acid solution (or a mixture) with a high yield.

20 Claims, No Drawings

PROCESS FOR CRYSTALLIZING NALMEFENE HYDROCHLORIDE

The present disclosure relates to an improved process for crystallizing nalmefene hydrochloride in a hydrated form.

BACKGROUND

Nalmefene is an opioid receptor antagonist that can inhibit pharmacological effects of both administered opioid agonists and endogenous produced agonists from the opioid system. The clinical usefulness of nalmefene as an antagonist comes from its ability to promptly and selectively reverse the effects of these opioid agonists, including the often-observed depressions in the central nervous system and the respiratory system.

Nalmefene has primarily been developed for use in the management of alcohol dependence, where it has shown good effect in doses of 10 to 40 mg taken when the patient believed drinking to be imminent (about 1-2 hours before drinking) (Karhuvaara et al., Alcohol. Clin. Exp. Res. 31(7): 1179-1187 (2007)). Additionally, nalmefene has also been investigated for the treatment of other addictions such as pathological gambling and addiction to shopping.

Nalmefene can be produced according to the method described by, for example, Hahn et al. (J. Med. Chem. 18:259-262 (1975)), Mallinckrodt (U.S. Pat. No. 4,751,307), and Meltzner et al. (U.S. Pat. No. 4,535,157). By using these methods, the free base of nalmefene is obtained, which can subsequently be converted into its hydrochloride salt, by use of conventional methods.

Nalmefene hydrochloride (HCl) monohydrate can be recrystallized in water. See, e.g., CN 106167492, U.S. Publ. Appl. No. 2014/0296525 A1, RU 2712232, and U.S. Pat. No. 8,598,352 describing procedures recrystallizing nalmefene HCl monohydrate in about 1.3 volumes of water with heating at about 60° C. and cooling to 0° C., and then isolating. These references do not describe the use of co-solvents or antisolvents. The yields are reported to be between 60% and 70%.

U.S. Pat. No. 8,754,217 B2 appears to describe the preparation of nalmefene HCl monohydrate by recrystallization in water with a limited hold time (2 hours) at 20° C. prior to isolation at 4° C. (Example 2.1a). The patent suggests that the dihydrate is formed similarly, except for being held at 20° C. for 2.5 days prior to isolation (Examples 1.1a and 1.1b). Alternatively, the dihydrate can be formed from seeding a recrystallization with the dihydrate form (Example 3).

In many cases, additional process steps after the isolation of nalmefene HCl monohydrate are employed to recover nalmefene from mother liquors. For example, the mother liquors are extracted with an organic solvent to remove some of the phosphine oxide impurities, concentrated, and more material is obtained (see e.g., WO 2013/083685). In some processes, the mother liquors are basified, nalmefene free base is extracted into organic solvents, and then hydrogen chloride is added to form the HCl salt (see e.g., U.S. Pat. No. 8,754,217 B2). In some processes, the mother liquors are basified, nalmefene free base is extracted into organic solvents, the nalmefene base is recovered, and then the HCl salt is re-formed in water. However, using organic solvents in the purification process can form additional impurities, e.g., forming solvates, which need to be removed or converted in later steps.

Accordingly, there is still a need for an effective and improved process for crystallizing nalmefene HCl monohydrate with high yield and purity.

BRIEF SUMMARY OF THE INVENTION

The present disclosure provides a novel and efficient process for crystallizing nalmefene HCl in a hydrated form.

An aspect of the present disclosure is directed to a process for crystallizing nalmefene hydrochloride, said process comprising:

mixing a source of nalmefene, water and hydrochloric acid to provide a substantially homogeneous mixture, wherein the hydrochloric acid is present in an amount sufficient to achieve a final molarity in the substantially homogeneous mixture at about 3 M to about 4 M; and crystallizing nalmefene hydrochloride from said substantially homogeneous mixture to provide a heterogenous mixture comprising a crystalline hydrated form of nalmefene hydrochloride in an acidic aqueous continuous phase.

In some embodiments, the process for crystallizing nalmefene hydrochloride comprises:

mixing said source of nalmefene in water or aqueous hydrochloric acid at an elevated temperature to obtain a substantially homogeneous mixture; and crystallizing nalmefene hydrochloride by adding concentrated hydrochloric acid to said substantially homogeneous mixture in an amount to achieve a final molarity of the hydrochloric acid at from about 3 M to about 4 M, thus providing a heterogeneous mixture comprising a crystalline hydrated form of nalmefene hydrochloride in an acidic aqueous continuous phase.

In some embodiments, the process for crystallizing nalmefene hydrochloride comprises:

mixing said source of nalmefene in an about 3 M to about 4 M hydrochloric acid at an elevated temperature to obtain a substantially homogeneous mixture; and cooling said substantially homogeneous mixture or allowing said substantially homogeneous mixture to cool to a reduced temperature to provide a heterogeneous mixture comprising crystalline hydrated form of nalmefene hydrochloride in an acidic aqueous continuous phase, wherein about 1 ml to about 5 ml of said acidic aqueous continuous phase is provided for every gram of said source of nalmefene.

In some embodiments, about 1 ml to about 3 ml of the acidic aqueous continuous phase is provided for every gram of said source of nalmefene. In some embodiments, about 2 ml of the acidic aqueous continuous phase is provided for every gram of said source of nalmefene.

The process of the disclosure comprises isolating said crystalline hydrated form of nalmefene hydrochloride from said heterogeneous mixture. In some embodiments, the way of isolation is filtration.

In some embodiments, the source of nalmefene is nalmefene free base. In some embodiments, the source of nalmefene is an acid salt of nalmefene. In some embodiments, said source of nalmefene is nalmefene hydrochloride. In some embodiments, said source of nalmefene is a hydrated form of nalmefene hydrochloride. In some embodiments, said hydrated form of nalmefene hydrochloride is nalmefene hydrochloride monohydrate. In some embodiments, said hydrated form of nalmefene hydrochloride is nalmefene hydrochloride dihydrate.

In some embodiments, said crystalline hydrated form of nalmefene hydrochloride provided by the process of the disclosure is crystalline nalmefene hydrochloride monohydrate.

In some embodiments, said crystalline hydrated form of nalmefene hydrochloride provided by the process of the disclosure is crystalline nalmefene hydrochloride dihydrate.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

The headings provided herein are not limitations of the various aspects of the disclosure, which can be defined by reference to the specification as a whole. It is also to be understood that the terminology used herein is for the purpose of describing particular aspects only, and is not intended to be limiting, since the scope of the present disclosure will be limited only by the appended claims.

Definitions

For convenience, the meaning of some terms and phrases used in the specification, examples, and appended claims are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

The articles "a," "an," and "the" are used herein to refer to one or to more than one (i.e., to at least one) of the grammatical object of the article. By way of example, "an element" means one element or more than one element.

As used herein, the term "about" means±10% of the specified value, unless otherwise indicated.

The term "at least" prior to a number or series of numbers is understood to include the number adjacent to the term "at least", and all subsequent numbers or integers that could logically be included, as clear from context. When at least is present before a series of numbers or a range, it is understood that "at least" can modify each of the numbers in the series or range.

As used herein, the terms "comprises," "comprising," "having," "including," "containing," and the like are open-ended terms meaning "including, but not limited to." To the extent a given embodiment disclosed herein "comprises" certain elements, it should be understood that present disclosure also specifically contemplates and discloses embodiments that "consist essentially of" those elements and that "consist of" those elements.

As used herein the terms "consists essentially of," "consisting essentially of," and the like are to be construed as semi-closed terms, meaning that no other ingredients which materially affect the basic and novel characteristics of an embodiment are included.

As used herein, the terms "consists of," "consisting of," and the like are to be construed as closed terms, such that an embodiment "consisting of" a particular set of elements excludes any element, step, or ingredient not specified in the embodiment.

As used herein, the term "nalmefene" refers to a compound having the chemical name of 17-(cyclopropylmethyl)-4,5α-epoxy-6-methylenemorphinan-3,14-diol, as illustrated by the following chemical structure:

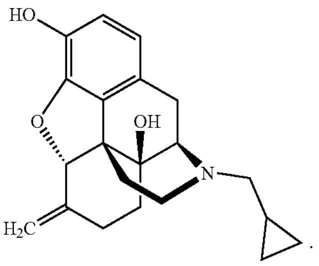

As used herein, the term "source of nalmefene" refers to a chemical material from which nalmefene free base, nalmefene salt and/or a solvate thereof, or a mixture thereof can be derived. Thus, a source of nalmefene can be a chemical material containing nalmefene free base or a salt of nalmefene (such as nalmefene hydrochloride (HCl)), or a solvate thereof, and any mixtures thereof. In some embodiments, the source of nalmefene is a solvate, such as a hydrate of a nalmefene salt. In some embodiments, the source of nalmefene is a hydrate of nalmefene HCl, such as nalmefene HCl monohydrate.

The term "substantially homogeneous mixture" as used herein means that the mixture is being largely but not necessarily wholly homogeneous.

The term "homogeneous mixture" as used herein refers to a mixture of uniform structure or composition throughout. The term encompasses solutions where there is complete miscibility between solute and the solvent at a given temperature. A solution is a apparent or clear homogeneous mixture, in which the solute particles are not visible and do not settle down in a noticeable way. The term homogeneous mixture also encompasses colloids, that is, a colloidal suspension of solute particles, typically smaller than 1000 nm dispersed in the solvent. Like a solution, the solute particles do not separate out.

The term "heterogenous mixture" as used herein refers to a mixture of non-uniform structure or composition. The term encompasses suspensions of insoluble solid particles that are dispersed in a liquid medium. The solute particles can be evenly dispersed in the medium but if left undisturbed the solute particles that range from 0.5 to m tend to settle down and can be separated from the solution by filtration or centrifugation.

The term "aqueous composition," as used herein, refers to an aqueous composition that can be an aqueous solution or an aqueous slurry.

As used herein, the term "solution" refers to a special type of homogeneous mixture composed substantially of one phase of two or more substances. In such a mixture, a solute is a substance dissolved in another substance, known as a solvent. The solution usually has the state of the solvent when the solvent is the larger fraction of the mixture.

The term "aqueous solution" refers to a solution in which the solvent is water.

As used herein, the term "slurry" is a heterogeneous mixture of solids denser than water suspended in liquid, usually water.

The term "slurrying," as used herein, refers to the act of converting a solid into a slurry.

As used herein, the term "aqueous slurry" is an aqueous heterogeneous mixture of solids denser than water. An aqueous slurry can contain solid particles and dissolved material.

The term "slurry-washing," as used herein, refers to purification of solids from contaminating materials with a solvent, such as water, with minimal dilution.

As used herein, the term "solid" refers to one of the four fundamental states of matter (the others being liquid, gas and plasma). The molecules in a solid are closely packed together and contain the least amount of kinetic energy. A solid is characterized by structural rigidity and resistance to a force applied to the surface. Unlike a liquid, a solid object does not flow to take on the shape of its container, nor does it expand to fill the entire available volume like a gas. The atoms in a solid are bound to each other, either in a regular geometric lattice (crystalline solids), or irregularly (an amorphous solid).

The term "pharmaceutically acceptable salt" refers to a salt prepared from pharmaceutically acceptable inorganic and organic acids. The present disclosure includes all non-toxic pharmaceutically acceptable salts of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like. Exemplary pharmaceutically acceptable acid addition salts include, without limitation, hydrochloric, hydrobromic, hydroiodic, sulfuric, phosphoric, formic, acetic, trifluoroacetic, propionic, citric, and benzoic acid salts.

Acid addition salts can be formed by mixing a solution of a particular compound with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound with a solution of a pharmaceutically acceptable non-toxic base such as sodium hydroxide, potassium hydroxide, lithium hydroxide, choline hydroxide, sodium carbonate and the like.

The term "solvate" as used herein is a combination, physical association and/or solvation of a biologically active compound (e.g., nalmefene or its salt) with a solvent molecule such as, e.g. a disolvate, monosolvate or hemisolvate, where the ratio of solvent molecule to compound of the present invention is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure may be present as solvated forms with a pharmaceutically acceptable solvent, such as water, methanol, ethanol, and the like, and it is intended that the present disclosure includes both solvated and unsolvated forms of compounds of the disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem. Commun.:* 603-604 (2001). A typical, non-limiting, process of preparing a solvate would involve dissolving a compound in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate. Some of the compounds disclosed herein may contain one or more asymmetric centers and may thus give rise to enantiomers, diastereomers, and other stereoisomeric forms, such as epimers. The present disclosure is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

The term "polymorph" as used herein refers to a crystalline form of a compound or a salt, hydrate, or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a salt, co-crystal, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. See, e.g., *Remington's Pharmaceutical Sciences,* $18^{th}$ ed., Mack Publishing, Easton PA, 173 (1990); *The United States Pharmacopeia,* $23^{rd}$ ed., 1843-1844 (1995) (incorporated herein by reference).

Crystalline forms are most commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed, or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. Moreover, instrument variation and other factors can affect the 2-theta values. A skilled artisan understanding these variations is capable of discriminating or ascertaining the defining features or characteristics of a particular crystal form using XRPD, as well as using other known physicochemical techniques.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral stereogenic centers present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

As used herein, the term "solvent" refers to a liquid substance that dissolves a solute, resulting in a solution. Water is a solvent for polar molecules and the most common solvent used by living things.

The term "concentrated hydrochloric acid" refers to 12 M or about 37% hydrochloric acid in water.

As used herein, the term "aqueous hydrochloric acid" is concentrated hydrochloric acid diluted with water. For example, an aqueous hydrochloric acid can be about 1 M, about 1.5 M, about 2 M, about 2.5 M, about 3 M, about 3.5 M, about 4 M, about 4.5 M, about 5 M, about 5.5 M, about 6 M, or about 6.5 M hydrochloric acid. In some embodiments, an aqueous hydrochloric acid is about 3 M to about 4 M hydrochloric acid. In some embodiments, an aqueous hydrochloric acid is 3.5 M hydrochloric acid. In some embodiment, an aqueous hydrochloric acid is 3.5 M hydrochloric acid.

As used herein, the term "acidic aqueous continuous phase" refers to the liquid phase of the heterogeneous mixtures described herein within which solid particles are distributed.

Processes of the Disclosure

The present inventor(s) come forth here with an efficient process, through which nalmefene HCl can be effectively crystallized from an aqueous hydrochloric acid solution (or mixture) as a crystalline hydrated form of nalmefene HCl with high yield and purity. The starting material can be any source of nalmefene. Using hydrochloric acid as an antisolvent without introduction of any organic solvents (that may form solvates of nalmefene HCl) minimizes the risk of adding additional impurities into the crystallized product. Residual hydrochloric acid can be evaporated during the product drying. The crystallization process described herein for crystallizing nalmefene HCl is expected to be applicable for large scale and affording crystalline hydrate form of nalmefene HCl in a high yield.

The present disclosure provides a process for crystallizing nalmefene hydrochloride, comprising:

- mixing a source of nalmefene, water and hydrochloric acid to provide a substantially homogeneous mixture, wherein the hydrochloric acid is present in the substantially homogeneous mixture in an amount sufficient to achieve a final molarity of about 3 M to about 4 M; and
- crystallizing the nalmefene hydrochloride to provide a heterogenous mixture comprising a crystalline hydrated form of nalmefene hydrochloride in an acidic aqueous continuous phase.

The source of nalmefene can be nalmefene free base, nalmefene salt and/or a solvate thereof, or a mixture thereof. In some embodiments, a source of nalmefene is nalmefene free base. In some embodiments, the source of nalmefene is a salt of nalmefene, such as nalmefene hydrochloride (HCl), or a solvate of nalmefene, or any mixtures thereof. In some embodiments, the source of nalmefene is a solvate of nalmefene salt, such as a hydrate of nalmefene salt. In some embodiments, the source of nalmefene is a hydrate of nalmefene HCl, such as nalmefene HCl monohydrate or nalmefene HCl dihydrate.

In some embodiments, the process further comprises filtering the substantially homogeneous mixture to remove trace impurities prior to crystallization.

In some embodiments, the process further comprises isolating a crystalline form of nalmefene hydrochloride from the heterogeneous mixture. In some embodiments, the crystalline form of nalmefene hydrochloride is isolated by filtration.

In some aspects, the process for crystallizing nalmefene hydrochloride comprises:

- mixing the source of nalmefene in water or aqueous hydrochloric acid at an elevated temperature to obtain a substantially homogeneous mixture; and
- adding concentrated hydrochloric acid to the substantially homogeneous mixture in an amount sufficient to achieve a final molarity of from about 3 M to about 4 M to provide the heterogeneous mixture comprising a crystalline hydrated form of nalmefene hydrochloride in an acidic aqueous continuous phase.

In some embodiments, the substantially homogeneous mixture is a solution or colloidal suspension of nalmefene HCl in aqueous solvent. In some embodiments, the nalmefene HCl is dissolved in the aqueous medium. In some embodiments, the nalmefene HCl exists as a colloid in the aqueous medium.

In some embodiments, about 1 ml to about 5 ml of an acidic aqueous continuous phase is provided for every gram of the source of nalmefene. In some embodiments, about 1 ml to about 3 ml of the acidic aqueous continuous phase is provided for every gram of the source of nalmefene. In some embodiments, about 2 ml of the acidic aqueous continuous phase is provided for every gram of the source of nalmefene.

In some embodiments, the process further comprises filtering the substantially homogeneous mixture (e.g., solution) prior to addition of the concentrated hydrochloric acid to remove trace solid impurities.

In some embodiments, the concentrated hydrochloric acid is added to the substantially homogeneous mixture (e.g., solution) in an amount to achieve a final molarity of about 3.5 M. In some embodiments, the concentrated hydrochloric acid is added to the substantially homogeneous mixture (e.g., solution) gradually to facilitate a slow, controlled crystallization process. For example, the concentrated hydrochloric acid can be added to the substantially homogeneous mixture (e.g., solution) within a period of at least 10 or 15 minutes.

In some aspects, the process for crystallizing nalmefene hydrochloride comprises:

mixing the source of nalmefene in about 3 M to about 4 M hydrochloric acid at an elevated temperature to obtain a substantially homogeneous mixture; and cooling the substantially homogeneous mixture or allowing the substantially homogeneous mixture to cool to a reduced temperature to provide a heterogenous mixture comprising crystalline hydrated form of nalmefene hydrochloride in an acidic aqueous continuous phase, wherein about 1 ml to about 5 ml of the acidic aqueous continuous phase is provided for every gram of the source of nalmefene.

In some embodiments, the substantially homogeneous mixture (e.g., solution) is allowed to cool. In other embodiments, the substantially homogeneous mixture is actively cooled.

In some embodiments, about 1 ml to about 3 ml of the acidic aqueous continuous phase is provided for every gram of the source of nalmefene. In some embodiments, about 2 ml of the acidic aqueous continuous phase is provided for every gram of the source of nalmefene.

In some embodiments, the aqueous hydrochloric acid is about 3.0 M, about 3.1 M, about 3.2 M, about 3.3 M, about 3.4 M, about 3.5 M, about 3.6 M, about 3.7 M, about 3.8 M, about 3.9 M, or about 4.0 M. In some embodiments, the aqueous hydrochloric acid is about 3.5 M.

In some embodiments of these aspects of the disclosure, the process further comprises isolating the crystalline hydrated form of nalmefene hydrochloride from the heterogeneous mixture. In some embodiments, the crystalline hydrated form of nalmefene hydrochloride is isolated by filtration.

In some embodiments, the source of nalmefene is nalmefene free base.

In some embodiments, the source of nalmefene is an acid salt of nalmefene. In some embodiments, the source of nalmefene is nalmefene hydrochloride.

In some embodiments, the source of nalmefene is a hydrated form of nalmefene hydrochloride. In some embodiments, the hydrated form of nalmefene hydrochloride is nalmefene hydrochloride monohydrate. In some embodiments, the hydrated form of nalmefene hydrochloride is nalmefene hydrochloride dihydrate.

In some embodiments, the source of nalmefene is dissolved at an elevated temperature of from about 50° C. to about 90° C. After the source of nalmefene has dissolved, the solution is allowed to cool to a reduced temperature. In some embodiments, the reduced temperature is from about 0° C. to about 15° C. In some embodiments, the solution is cooled to about 0° C. to about 5° C. and the crystalline hydrated form of nalmefene hydrochloride is isolated. In some embodiments, the isolation is by filtration.

In some embodiments, the process of the disclosure further comprises steps of washing the isolated crystalline hydrated form of nalmefene hydrochloride with aqueous hydrochloric acid, such as 3 M hydrochloric acid, and drying.

In some embodiments, the process of the disclosure provides a crystalline hydrated form of nalmefene hydrochloride that is crystalline nalmefene hydrochloride monohydrate.

In some embodiments, the process of the disclosure provides a crystalline hydrated form of nalmefene hydrochloride that is crystalline nalmefene hydrochloride dihydrate.

EXAMPLES

The process for crystallizing described herein is now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1

Solubility Studies in Aqueous HCl Solution

A series of nalmefene HCl monohydrate solubility experiments were carried out in aqueous HCl. Nalmefene HCl monohydrate (520 mg) was charged to a 4 mL capped vial, followed by solvent (0-6 M HCl, 780 μL, 1.5 volumes) and heated to 80° C. on a pie-block. Increasing amounts of solvent were added periodically until dissolution was achieved (determined visually).

Seven dissolution experiments were carried out. The results are summarized in Table 1 below:

TABLE 1

Solubility of Nalmefene HCl at 80° C.

| Sample No. | HCl molarity | Volumes needed to dissolve nalmefene HCl at 80° C. |
|---|---|---|
| 0 | 0 (water) | Fewer than 1.5 |
| 1 | 1 | 1.5 |
| 2 | 2 | 2.5 |
| 3 | 3 | 6.5 |
| 4 | 4 | 6.5 |
| 5 | 5 | 4.0 |
| 6 | 6 | 3.5 |

It is believed that HCl acts as an antisolvent for nalmefene HCl monohydrate in water. The results in Table 1 show that nalmefene HCl monohydrate had a minimum solubility in 3-4 M HCl. Therefore, additional recrystallizations of nalmefene HCl monohydrate were carried out in 3.5-3.6 M HCl and are described in Example 2 below.

Example 2

Crystallization of Nalmefene HCl Monohydrate

The same starting material nalmefene HCL monohydrate was used in the following crystallization experiments in 3.5-3.6 M HCl:

(a) Recrystallization of Nalmefene HCl from 3.6 M Aqueous HCl (Five Volumes):

Nalmefene HCl monohydrate (10.00 g, 4% water, 9.60 g anhydrous) was charged to a 100 mL round bottom flask and water (35 mL, 3.5 volumes) was added. The slurry was heated to 50° C., and completely dissolved at 33° C. Concentrated HCl (12 M, 15 mL) was added over 15 minutes at a rate so that the temperature did not exceed 55° C. Seeds were added after 5 mL of HCl was added, and the solution became a slurry. The slurry was allowed to cool to room temperature, and then further cooled on ice for one hour. The mixture was filtered, and the solids were slurry-washed with cold 3 N HCl (20 mL), and filtered. The solids were air-dried to a constant weight of to obtain Sample A of nalmefene HCl monohydrate (8.60 g, 8.86% water by KF, 82% yield adjusted for water content).

(b) Recrystallization Nalmefene HCl from 3.5 M Aqueous HCl (Three Volumes):

Nalmefene HCl monohydrate (20.00 g, 4% water, 19.20 g anhydrous) was charged to a 100 mL round bottom flask and water (42.5 mL) was added. The slurry was heated to 50° C., and completely dissolved at 47° C. Concentrated HCl (12 M, 17.5 mL) was added over 10 minutes at a rate so that the temperature did not exceed 55° C. The reaction self-seeded after 5 mL of HCl was added, and the solution became a slurry. The slurry was allowed to cool to room temperature, and then further cooled on ice for one hour. The mixture was filtered, and the solids were washed with cold 3 N HCl (20 mL), and filtered. The solids were split into two equal portions by weight. One portion was air-dried to a constant weight to obtain Sample B1 of nalmefene HCL monohydrate (9.31 g, 7.98% water by KF, 89% adjusted for water content). The second portion was dried in a 70° C. vacuum drying oven overnight and then allowed to equilibrate open to the air to a constant weight to obtain Sample B2 of nalmefene hydrochloride monohydrate (9.27 g, 6.27% water by KF, 90% yield adjusted for water content).

(c) Recrystallization from 3.5 M Aqueous HCl (Two Volumes):

Nalmefene HCl monohydrate (20.00 g, 4% water, 19.20 g anhydrous) was charged to a 100 mL round bottom flask and water (28.3 mL) was added. The slurry was heated to 55° C. to afford a solution. Concentrated HCl (12 M, 11.7 mL) was added over 10 minutes at a rate so that the temperature did not exceed 57° C. The reaction self-seeded after 5 mL of HCl was added, and the solution became a slurry. The slurry was allowed to cool to room temperature, and then further cooled on ice for one hour. The mixture was filtered, and the solids were washed with cold 3 N HCl (15 mL), and filtered. The solids were dried in a 70° C. vacuum drying oven overnight and then allowed to equilibrate open to the air to a constant weight to obtain Sample C of nalmefene HCl monohydrate (18.44 g, 5.57% water by KF, 91% yield adjusted for water content).

Results

The water-corrected yields of the three experiments above are tabulated in Table 2 below:

TABLE 2

Isolated Yields of Nalmefene HCl Recrystallized from 3.5M and 3.6M HCl

| Sample | Recrystallization volume | HCl Molarity | Isolated Yield corrected for water content |
|---|---|---|---|
| A | 5 | 3.6 | 82% |
| B2 | 3 | 3.5 | 90% |
| C | 2 | 3.5 | 91% |

Based on the Samples B1 and B2, oven drying the product followed by equilibration open to the air resulted in approximately the same level of hydration as an air-dried sample. The yields represent a significant improvement over the yields reported in the literature for water (see, e.g., U.S. Pat. No. 8,754,217, Examples 2.1a and 2.1b providing yields of 61% and 67%, respectively, for nalmefene HCl monohydrate, and Example 3 providing a calculated yield of 68% for nalmefene HCl dihydrate).

Crystallization of nalmefene HCl monohydrate in two volumes of 3.5 N HCl resulted an 91% isolated yield (Sample C). In view of the above, the process of the disclosure is scalable. The isolated nalmefene HCl appears to be the monohydrate based on water content determined by Karl-Fisher titration. The XRPD spectrum of Sample C matched the literature diffraction pattern for the monohydrate, published in U.S. Pat. No. 8,754,217.

Having now fully described this disclosure, it will be understood by those of ordinary skill in the art that the same can be performed within a wide and equivalent range of conditions, formulations, and other parameters without affecting the scope of the invention or any embodiment thereof.

Other embodiments of the disclosure will be apparent to those skilled in the art from consideration of the specification and practice of the invention disclosed herein. It is intended that the specification be considered exemplary only, with a true scope and spirit of the invention being indicated by the following claims.

All patents, patent applications, and publications cited herein are fully incorporated by reference herein in their entirety.

What is claimed is:

1. A process for crystallizing nalmefene hydrochloride, said process comprising:

mixing a source of nalmefene, water and hydrochloric acid to provide a substantially homogeneous mixture, wherein the hydrochloric acid is present in said substantially homogeneous mixture in an amount sufficient to achieve a final molarity of about 3 M to about 4 M; and crystallizing said nalmefene hydrochloride from said substantially homogeneous mixture to provide a heterogenous mixture comprising crystalline hydrated form of nalmefene hydrochloride in an acidic aqueous continuous phase.

2. The process of claim 1, further comprising filtering said substantially homogeneous mixture to remove trace impurities prior to said crystallizing.

3. The process of claim 1, further comprising isolating a crystalline form of nalmefene hydrochloride from said heterogeneous mixture.

4. The process of claim 1, wherein said process comprises:

mixing said source of nalmefene in water or aqueous hydrochloric acid at an elevated temperature to obtain a substantially homogeneous mixture; and crystallizing nalmefene hydrochloride by adding concentrated hydrochloric acid to said substantially homogeneous mixture in an amount sufficient to achieve a final molarity of the hydrochloric acid of from about 3 M to about 4 M, thus providing a heterogeneous mixture comprising a crystalline hydrated form of nalmefene hydrochloride in an acidic aqueous continuous phase.

5. The process of claim 4, wherein about 1 ml to about 5 ml of an acidic aqueous continuous phase is provided for every gram of said source of nalmefene.

6. The process of claim 4, further comprising filtering said substantially homogeneous mixture to remove trace solid impurities.

7. The process of claim 4, wherein said concentrated hydrochloric acid is added to said substantially homogeneous mixture in an amount to achieve a final molarity of about 3.5 M.

8. The process of claim 1, wherein said process comprises:

mixing said source of nalmefene in about 3 M to about 4 M hydrochloric acid at an elevated temperature to obtain a substantially homogeneous mixture; and cooling said substantially homogeneous mixture or allowing said substantially homogeneous mixture to cool to a reduced temperature to provide a heterogeneous mixture comprising crystalline hydrated form of nalmefene hydrochloride in an acidic aqueous continuous phase, wherein about 1 ml to about 5 ml of an acidic aqueous continuous phase is provided for every gram of said source of nalmefene.

9. The process of claim 4, wherein said crystalline hydrated form of nalmefene hydrochloride is isolated from said heterogeneous mixture.

10. The process of claim 1, wherein said source of nalmefene is nalmefene free base.

11. The process of claim 1, wherein said source of nalmefene is an acid salt of nalmefene.

12. The process of claim 11, wherein said source of nalmefene is nalmefene hydrochloride.

13. The process of claim 12, wherein said source of nalmefene is a hydrated form of nalmefene hydrochloride.

14. The process of claim 13, wherein said hydrated form of nalmefene hydrochloride is nalmefene hydrochloride monohydrate or nalmefene hydrochloride dihydrate.

15. The process of claim 4, wherein said source of nalmefene is dissolved at a temperature of from about 50° C. to about 90° C.

16. The process of claim 4, further comprising allowing said substantially homogeneous mixture to cool to a reduced temperature.

17. The process of claim 16, further comprising cooling said mixture to about 0 to 5° C., and isolating said crystalline hydrated form of nalmefene hydrochloride by filtration.

18. The process of claim 17, further comprising steps of washing said isolated crystalline hydrated form of nalmefene hydrochloride with 3 M hydrochloric acid, and drying.

19. The process of claim 1, wherein said crystalline hydrated form of nalmefene hydrochloride is crystalline nalmefene hydrochloride monohydrate.

20. The process of claim 1, wherein said crystalline hydrated form of nalmefene hydrochloride is crystalline nalmefene hydrochloride dihydrate.

* * * * *